(12) United States Patent
Kim et al.

(10) Patent No.: US 9,513,280 B2
(45) Date of Patent: Dec. 6, 2016

(54) MICROFLUIDIC BIOLOGICAL BARRIER MODEL AND ASSOCIATED METHOD

(71) Applicant: The University of Utah Research Foundation, Salt Lake City, UT (US)

(72) Inventors: Hanseup Kim, Salt Lake City, UT (US); Ross Booth, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 14/012,781

(22) Filed: Aug. 28, 2013

(65) Prior Publication Data

US 2014/0065660 A1 Mar. 6, 2014

Related U.S. Application Data

(60) Provisional application No. 61/694,089, filed on Aug. 28, 2012.

(51) Int. Cl.
| | |
|---|---|
| *G01N 33/50* | (2006.01) |
| *C12M 1/42* | (2006.01) |
| *B01L 3/00* | (2006.01) |
| *C12M 3/06* | (2006.01) |

(52) U.S. Cl.
CPC .......... *G01N 33/5064* (2013.01); *C12M 35/08* (2013.01); *G01N 33/5058* (2013.01); *B01L 3/502746* (2013.01); *C12M 23/16* (2013.01)

(58) Field of Classification Search
CPC ... C12M 35/08; C12M 23/16; G01N 33/5058; G01N 33/5064; B01L 3/502746
USPC ...................................... 435/297.2
See application file for complete search history.

(56) References Cited

U.S. PATENT DOCUMENTS

| | | | |
|---|---|---|---|
| 2004/0245102 A1* | 12/2004 | Gilbert et al. ................. | 156/60 |
| 2008/0064088 A1* | 3/2008 | Shuler et al. ............. | 435/294.1 |
| 2011/0104658 A1* | 5/2011 | Prabhakarpandian | G01N 33/5029 435/288.7 |
| 2011/0290113 A1* | 12/2011 | Borenstein et al. .......... | 156/230 |
| 2012/0149021 A1* | 6/2012 | Yung et al. ................ | 435/287.1 |
| 2012/0211373 A1* | 8/2012 | El-Sayed et al. ............ | 435/401 |

* cited by examiner

*Primary Examiner* — Gautam Prakash
(74) *Attorney, Agent, or Firm* — Stoel Rives LLP

(57) ABSTRACT

A biological barrier model is disclosed. In some embodiments the barrier may be configured to model the blood brain barrier. The model may include a membrane having one or more cell cultures disposed thereon. The cells cultures may be grown in the presence of shear stress induced by flow through the device in some embodiments. The size of the barrier, as well as the distance to electrodes and other sensors, may be in the microscale range. Further, in some embodiments the model may comprise an array of parallel channels and membranes.

15 Claims, 11 Drawing Sheets

MICROFLUIDIC BIOLOGICAL BARRIER MODEL AND ASSOCIATED METHOD

RELATED APPLICATION

This patent application claims the benefit of U.S. Provisional Patent Application No. 61/694,089, filed Aug. 28, 2012, the disclosure of which is herein incorporated by reference in its entirety.

TECHNICAL FIELD

The present disclosure relates generally to models of biological barriers. Specifically, the current disclosure relates to biological barrier models, such as models of the blood brain barrier, which may comprise dynamic microfluidic channels and cell cultures on membranes disposed between such channels.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

BACKGROUND

Figure 1:
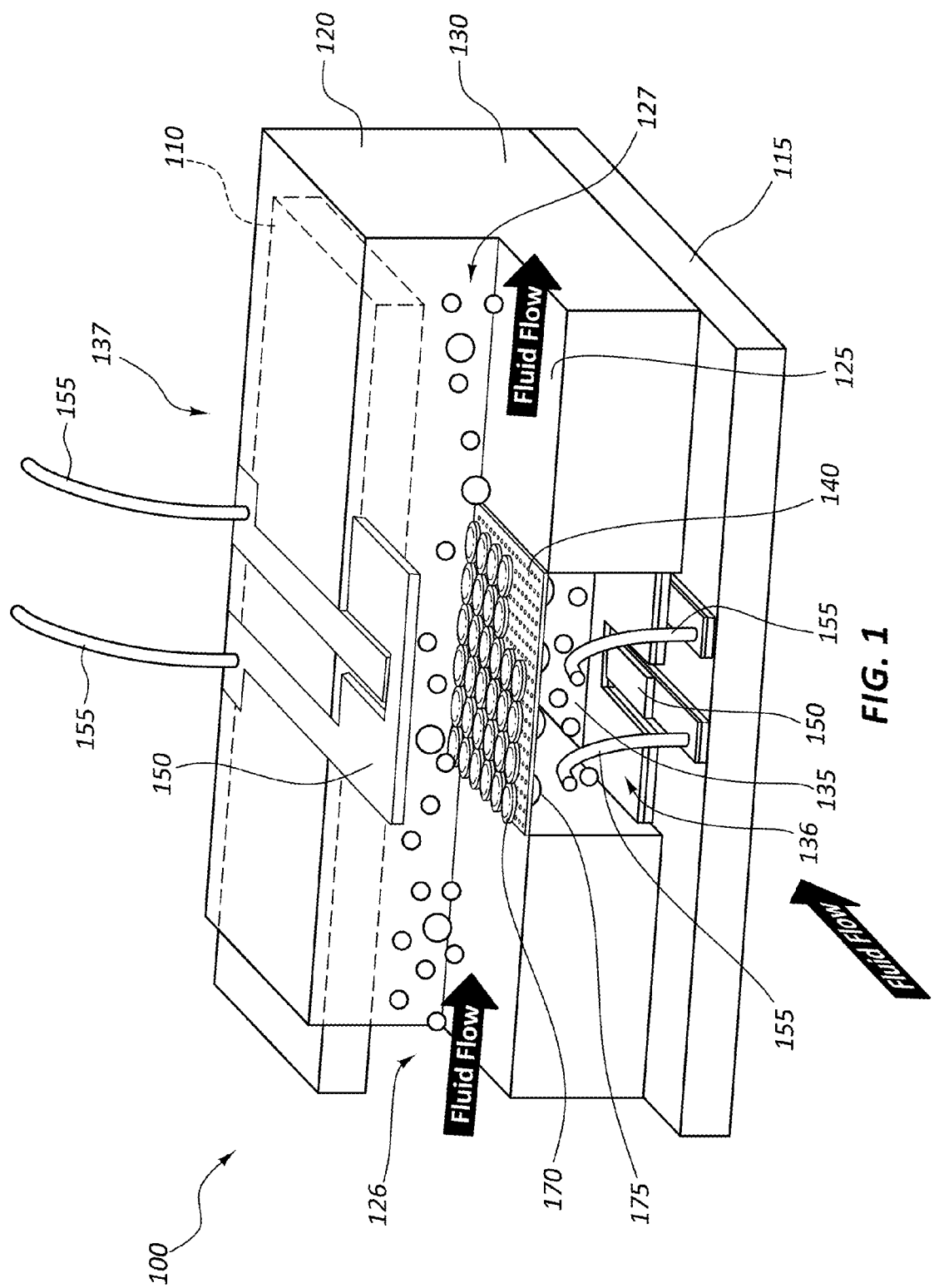
FIG. 1 is a 3D schematic illustration of one embodiment of a microfluidic blood brain barrier model (μBBB).

Diseases of the central nervous system (CNS) present a prevalent and ever-increasing burden for the world healthcare industry. For example, Alzheimer's disease is diagnosed in an estimated 24 million people, a number projected to double every 20 years. Despite such emerging demands for treatment of CNS diseases, only about 7% of CNS drugs in clinical development reach the marketplace, compared to the about 12% average across all therapeutic areas, or about 20% for cardiovascular drugs.

This low success rate is often attributed to a unique CNS structure coined as the blood-brain barrier (BBB), which introduces a pharmacokinetic hurdle by blocking compounds from entering brain tissues from capillaries. Only compounds smaller than about 500 Da easily cross the BBB, but few CNS diseases may consistently respond to this category of molecules.

Because the BBB blocks nearly all polar or large compounds, new drug treatments for the CNS of higher molecular weight must take BBB function into account, which, in turn, may require more extensive pre-clinical studies.

Detailed Description

The use of in vitro models of the BBB may augment the conventional pharmaceutical approach focusing on drug design, may help predict the penetration of drug candidates across the BBB, and may allow pre-screening and optimization of new treatments prior to animal and clinical studies. Additionally, BBB models may have further applications, such as, without limitation, utilization in studying the role of barrier function on CNS disease progression, use in testing methods of drug delivery, and other applications involving simulation or study of the BBB.

BBB studies are performed largely in two platforms: in vivo and in vitro models. In vivo models directly utilize entire living organisms, typically rats or mice, while in vitro models construct artificial environments with cultured cells to mimic in vivo structures. In vitro models may be a valuable pre-cursor to animal models due to factors such as: potentially lower cost, short time requirements, and ethical constraints relating to the use of live animals. Further, in vitro BBB models may enable controlled, repeatable, and non-invasive tests: permeability assays, resistance measurements, and microscopy, tests that may not be available in in vivo BBB applications.

Although traditional in vivo models may provide environments which are close to the human phenotype, they cannot provide massively-parallel, controlled, and repeatedly identical environments for reliable and quantitative studies. In terms of practicality, in vivo models may simply require extraordinary amounts of cost, time, and man-hours per test, in addition to potential ethical issues, as compared to in vitro alternatives.

In vitro models may significantly reduce such issues by creating identical environments in numerous arrays, may be available at a lower cost, may require less time, and may not be subject to the same ethical issues. Thus, the development and utilization of valid in vitro models may facilitate the overall drug development process by, for example, acting as a pre-cursor, or a replacement, for animal studies.

As used herein, the phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

Additionally, the term "microfluidic" as used herein relates to components where moving fluid is constrained in channels wherein one or more dimensions are 1 mm or smaller (microscale). Microfluidic channels may be larger than microscale in one or more directions, though the channel will be on the microscale in at least one direction. In some instances the geometry of a microfluidic channel may be configured to control the fluid flow rate through the channel. Microfluidic channels can be formed of various geometries to facilitate a wide range of flow rates through the channels.

The validity of an in vitro model may be evaluated based on how well it reproduces certain physiological and biological characteristics of its in vivo archetype. For example, characteristics of the BBB include: (1) the primary structure, consisting of strongly expressed tight junctions between endothelial cells which directly control compound permeability; (2) co-culture of endothelial cells with astrocytes including endfoot contact, which plays an important role in modulating barrier function through cell-cell signaling; (3) mechanotransductive effects of shear stress from fluid flow on endothelial cells, which influences cell differentiation and tight junction formation; (4) selective permeability from the constituted structures to dissolved compounds; (5) maintenance of high electrical resistance representing the maturity and soundness of the structures.

Various in vitro models have been developed to mimic some or all of these characteristics. In vitro models may be generally divided into two groups: static and dynamic models, wherein dynamic models include fluid flow, resulting in shear stress over the surface of the cells within the model. Static models, which were generally developed and implemented earlier than dynamic models, include transwell model setups. Dynamic in vitro BBB (DIV-BBB) models have also been developed, some of which utilize hollow fibers to mimic the BBB architecture and flow conditions, and to provide shear stress. In many such models, however, wall thickness (in some instances about 150 pm) may be significantly higher than transwell thickness (in some instances about 10 pm), which, in turn, may discourage cell-cell interaction. Additionally, DIV-BBBs may take significantly longer to reach steady-state trans-endothelial electrical resistance (TEER) values, as compared to static transwell models. DIV-BBB and transwell models are described and compared in: S. Santaguida, D. Janigro, M. Hossain, E. Oby, E. Rapp and L. Cucullo, *Brain Res.*, 2006, 1109, 1-13; Mini-Reviews in Medicinal Chemistry, 2010, Vol. 10, 263-271; and Recent Patents on CNS Drug Discovery, 2011, 6, 107-118; which are each herein incorporated by reference.

As further detailed below, a microfluidic BBB model according to the present disclosure (μBBB) may compare to in vivo and other in vitro static and dynamic BBB models as follows: (1) potentially lower costs and timescales than in vivo studies; (2) capability to produce massively-parallel, controlled and repeated environments that may not be available with in vivo models; (3) creation of a dynamic microenvironment that may provide shear stress stimulation to the cells and may allow improved analysis of test compounds and controlled delivery as compared to static models; and (4) potentially thinner culture membranes, which may decrease the distance between co-cultured cells as compared to DIV-BBB models. Additionally, the μBBB model may use smaller functional volumes for quicker media exchange and material conservation. Moreover, a μBBB model may facilitate shorter times to steady-state TEER levels which may allow a more rapid turn-around time, shortening experiments, and allowing a more high-throughput approach to experimentation. The μBBB model may also enable installation of high-density electrodes with relatively small (for example, about 200 μm in some embodiments) gaps between either electrode and the cell layers, with uniform ion flow density, which may minimize background resistance and error. Non-destructive microscopy of the system may also be possible depending on electrode placement, due to transparency of the substrate. In some embodiments the μBBB model may be polymer-based, thus allowing for comparatively rapid and low-cost fabrication. The table below provides a comparison summary of certain aspects of in vivo models, transwell in vitro models, DIV-BBB models, and one embodiment of a μBBB model according to this disclosure.

TABLE 1

Comparison of various BBB models

| | In vivo models | In vitro models | | |
|---|---|---|---|---|
| Experimental system | Animals | Transwells | DIV-BBB | μBBB |
| Relative cost | High | Very Low | Low | Low |
| Massively-parallel, controlled, and repeatedly identical | No | Yes | Yes | Yes |
| Shear stress/dynamic flow | Yes | No | Yes | Yes |
| (Quantitative analysis) | (No) | — | (Yes) | (Yes) |
| Space between co-cultures | Immediate | <10 μm | >150 μm | <10 |
| Functional media volumes | N/A | 0.5-2 ml | 1.4 ml | 12 μl |
| Time to steady-state TEER | N/A | 3-4 days | 9-12 days | 3-4 days |
| TEER electrodes - Ion flow profile | Invasive | Uniform {EndOhm} | Non-uniform | Uniform |
| (Gap size) | | (<2 mm {EndOhm}) | (>1 cm) | (<400 μm) |
| (Fixed position) | | (No) | (Yes) | (Yes) |
| Non-destructive microscopy | No | Yes | No | Yes |
| Fabrication | N/A | Simple | Complex | Moderate |

As also detailed below, a μBBB model within the scope of this disclosure may comprise one or more of the following features. Capability to culture cells in the presence of flow to replicate shear stress on cells at the actual BBB. Disposition of various cells, such as endothelial cells and astrocytes, which are close enough to interact, though the cells may be separated by a membrane. Additionally, the model may be configured to allow measurement of concentrations of materials on both sides of the barrier. Furthermore, minimal distances between the barrier and the measurement apparatus may minimize noise or other errors in the measurements.

It will be readily understood by one of ordinary skill in the art having the benefit of this disclosure that the components of the embodiments, as generally described and illustrated in the figures herein, could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In some embodiments, a μBBB model within the scope of this disclosure may comprise a multi-layered microfluidic device. FIG. 1 is a 3D schematic illustration of one embodiment of a μBBB model 100. In the illustrated embodiment, the μBBB model 100 comprises a top glass layer 110 and a bottom glass layer 115. A PDMS luminal channel layer 120 and a PDMS abluminal channel layer 130 are disposed between the glass layers 110, 115. In the illustrated embodiment, the luminal channel layer 120 houses a luminal channel 125 disposed substantially perpendicularly to an abluminal channel 135 housed within the abluminal channel layer 130. These perpendicularly-crossing channels 125, 135 may be configured to introduce dynamic flows within the μBBB model 100. In the illustrated embodiment of FIG. 1, the two "Fluid Flow" arrows in luminal channel 125 indicate the direction of flow through the luminal channel 125, while the single "Fluid Flow" arrow positioned toward the bottom of FIG. 1 indicates the direction of flow through the abluminal channel 135.

Further, a semipermeable membrane 140 may be disposed between the luminal channel 125 and the abluminal channel 135. Thus, the membrane 140 may separate the luminal channel 125 and the abluminal channel 135 at the intersection of these channels. In some embodiments, and as further described below, various types of cells may be cultured on one or both sides of this membrane 140. The membrane 140 may comprise a polymer, including membranes comprised at least partially of polycarbonate, polyester, and collagen-coated polytetrafluoroethylene. Additionally, in some embodiments the membrane 140 may be porous, including membranes having an average pore diameter from about 0.2 μm to about 2.0 μm, including from about 0.2 μm to about 0.6 μm and membranes 140 with average pore diameters of no less than 0.4 μm in diameter. In some such embodiments the pore sizes may be configured to allow neurites to cross the membrane 140. In other embodiments the pores may be larger or smaller. In some embodiments, the membrane 140 may comprise track-etched pores. Additionally, the membrane 140 may have a nominal pore density of about $1\times10^8$ per $cm^2$, for pore sizes of about 0.4 μm. Furthermore, the membrane 140 may be less than 10 μm thick in some embodiments.

One or more electrodes 150 may be disposed or embedded in the device and may be configured to monitor TEER across the membrane 140 and any related cell cultures. In some embodiments the electrodes 150 may be disposed relatively close to the cell cultures, thus minimizing measurement noise or other interference. For example, in some embodiments the electrodes 150 are disposed within 200 μm of the cultures.

In some embodiments, the μBBB model 100 may comprise cell cultures on both sides of the membrane 140, while in other embodiments cells may be cultured only on one side of the membrane 140. Various cell types and cell lines may be used on one or both sides of the membrane in any combination. In the embodiment illustrated in FIG. 1, endothelial cells 170 are disposed on the upper, or luminal side, of the membrane 140 while astrocytes 175 are disposed on the lower, or abluminal side, of the membrane 140. As further detailed below, these cells 170, 175 may be co-cultured and may be disposed in such a manner as to approximate the cell densities and disposition of such cells in the BBB.

In some embodiments, the luminal channel 125 may be about 200 μm high, and 2 mm wide at the interface with the abluminal channel 135. The abluminal channel 135 may likewise be about 200 μm high and about 5 mm wide at the interface with the luminal channel 125. These dimensions may be configured to induce laminar flows within each channel 125, 135. The membrane 140 may thus be disposed at a junction between the two channels 125, 135 and may thus have an area of about 10 $mm^2$. Further, the luminal channel 125 may have a high aspect ratio (such as 10:1) to promote uniform shear stress distribution across cells cultured on the luminal side of the membrane 140 (such as endothelial cells 170, for example) and the abluminal channel 135 may be significantly wider to minimize shear stresses on cells cultured on the abluminal side of the membrane 140 (such as astrocytes 175, for example).

In some embodiments, a membrane 140 may be configured with large enough pores to encourage direct cell-cell contact between cell types, while not large enough to introduce problems with adhesion or cell migration through the membrane 140. Membranes of various materials, porosities, and permeability may be utilized within the scope of this disclosure. Suitable membranes include polycarbonate membranes, and may further include porous nanocrystalline silicon (pnc-Si), which, although only recently discovered, has been shown to be suitable for many biotechnology applications. Such pnc-Si membranes provide a desirable molecular thinness for the μBBB models of this disclosure. These porous membranes have been produced with thicknesses varying between 10 nm and about 50 nm. Since transport resistance generally scales in proportion to membrane thickness, pnc-Si membranes should perform better than other known membranes in such barrier transport models. Pores in pnc-Si membranes are formed by inducing silicon crystal growth in an amorphous layer, and pore size distribution is varied by the temperature at which crystallization is induced. Pore sizes can be tuned in this manner between 3 nm and 80 nm by adjusting the temperature of annealing. In some variations of this method, porosity can be up to 15%. Furthermore, pnc-Si membranes demonstrate other practical benefits including inexpensive and easily scaled manufacture. In some embodiments such membranes 140 may be relatively thin, to minimize the distance between cells on either side and thus potentially encourage cell-cell interaction across the membrane. The membrane 140 may thus be sufficiently permeable to allow certain elements to cross the membrane, and to allow cell interaction, while still maintaining sufficient structure to allow the cell cultures to adhere to the membrane 140.

The µBBB model 100 may further comprise one or more electrodes 150. The electrodes 150 may be configured to sense the composition or concentration of materials within the channels 125, 135. For example, in the illustrated embodiment, two sets of two AgCl thin-film TEER electrode 150 pairs form a four-point sensing structure on each side of the membrane 140. The areas of the electrodes 150 are designed to be proportional (75% in the illustrated embodiment) to the cell culture area of the membrane 140 in order to encourage uniformly distributed ion flow. In some instances this may encourage uniformly distributed ion flow across the area of the membrane 140 surface.

The microscale environment may further reduce noise or other errors in the measurement by minimizing the distance between the measuring electrodes 150 and the membrane 140. Additionally, the µBBB model 100 may be configured with fluidic and/or electrical connection points. For example, in the illustrated embodiment, there are two pairs of fluidic and electrical input/output connections, respectively, for connection points. Specifically, the µBBB model 100 of FIG. 1 comprises two sets of wires 155 extending from the electrodes 150, configured to provide input/output capability with the electrodes 150. Further, each channel 125, 135 may comprise an inlet 126, 136 and an outlet 127, 137 to facilitate introduction of flow through the channels 125, 135 or otherwise provide input/output capability. In various embodiments, the membrane 140 may be disposed as shown in FIG. 1, or flipped with the opposite sides disposed toward either channel 125, 135. The µBBB model 100 may be configured to allow flow in either direction through either channel 125, 135 and the µBBB model 100 may be configured to be reusable over various tests or runs.

Figure 2:
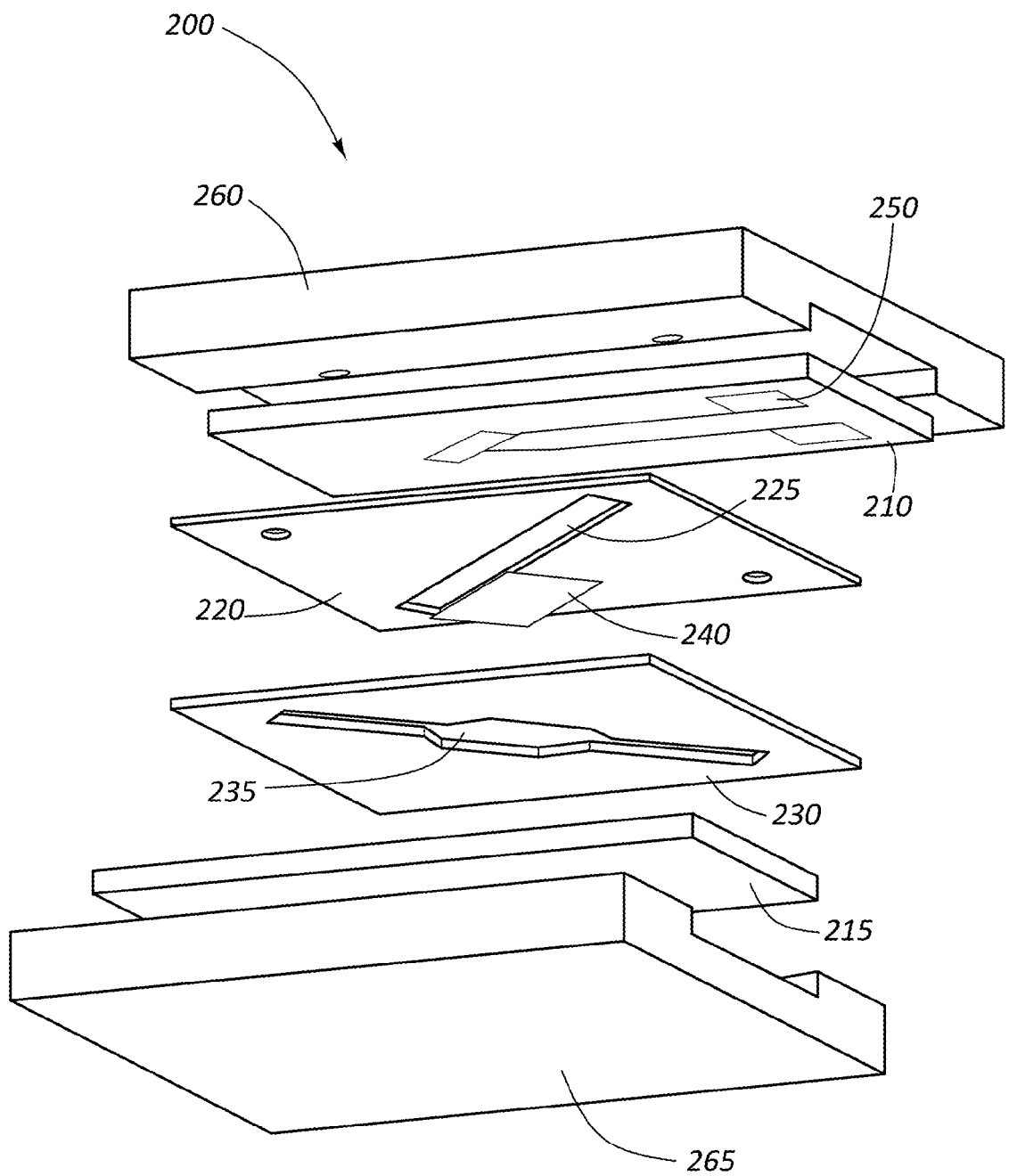
FIG. 2 is an exploded schematic view of another embodiment of a μBBB model.

In some embodiments, a µBBB model may be constructed by successively disposing various layers of material. For example, FIG. 2 is an exploded schematic view of a µBBB model 200 so constructed. The embodiment of FIG. 2 may include components that resemble components of FIG. 1 in some respects. For example, the embodiment of FIG. 2 includes a luminal channel layer 220 that may resemble the luminal channel layer 120 of FIG. 1. It will be appreciated that all the illustrated embodiments may have analogous features. Accordingly, like features are designated with like reference numerals, with the leading digits incremented to "2." Relevant disclosure set forth above regarding similarly identified features thus may not be repeated hereafter. Moreover, specific features of the µBBB model and related components shown in FIG. 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the µBBB model and related components of FIG. 2. Any suitable combination of the features, and variations of the same, described with respect to the µBBB model and components illustrated in FIG. 1, can be employed with the µBBB model and components of FIG. 2, and vice versa. This pattern of disclosure applies equally to further embodiments depicted in subsequent figures and described hereafter.

Again, FIG. 2 is an exploded schematic view of a µBBB model 200 that may comprise four PDMS substrates, two glass layers, and a porous polycarbonate membrane sandwiched at the center between the PDMS layers. More specifically, the µBBB model 200 of FIG. 2 comprises a first PDMS top layer 260, a top glass layer 210, a first channel layer 220, a membrane 240, a second channel layer 230, a bottom glass layer 215, and a bottom PDMS layer 265. These layers may be successively stacked on each other in the assembled µBBB model 200.

The glass layers 210, 215 may further comprise electrodes 250 and the channel layers 220, 230 may each comprise a channel 225, 235 disposed therein. In the illustrated embodiment, the upper channel layer 220 is associated with the luminal channel 225 and the lower channel layer 230 with the abluminal channel 235, though in other embodiments this order could be reversed. The membrane 240 may be positioned between the intersection of the channels 225, 235. Thus, in some embodiments, the µBBB 200 may be fabricated by sequentially bonding the four patterned PDMS sub-layers 260, 220, 230, 265, two embedded electrode layers 210, 215, and the sandwiched polycarbonate membrane 240, resulting in a fully integrated device.

Exemplary Device Fabrication

A µBBB according to this disclosure, analogous to the embodiments of FIGS. 1 and 2, was fabricated as follows. First, electrode layers were produced by cleaning 1 mm glass slides with piranha etch, and sputter depositing (Denton Discovery 18) thin-film electrodes with 20 nm Cr, 150 nm Au, and 800 nm Ag. Instachange marking film (3M) was patterned with a laser patterning system (Universal) to be used as a sputter mask. Silver surface was chlorinated chemically with $FeCl_3$ for 60 s at room temperature to generate an electrochemically active AgCl surface. Glass slides were diced (Disco DAD641) to 18 mm by 25 mm and embedded in 3 mm thick PDMS and cured at 65° C. for 2 h. Four I/O holes (0.5 mm) were cored in the top layers by punching.

To produce the channel feature layers, PDMS pre-polymer was spin-coated at 288 RPM for 1 min and cured at 65° C. for 2 h to produce 200 µm sheets and features were laser-patterned. Polycarbonate sheets (400 nm pores, 10 µm thick) were cut from transwells (Corning) to 5×10 mm rectangles. The top and bottom PDMS layers, the polycarbonate sheets, and the PDMS channel layers were bonded using spin-coated and stamped 50:50 ratio PDMS pre-polymer:toluene. Copper wire was bonded to bond-pads with silver epoxy for electrical connections. As with the embodiments of FIGS. 1 and 2, a porous membrane was disposed at the intersection of the channels.

In order to form a dual-layer BBB model on the chip, co-culture of endothelial and astrocytic cells was performed by seeding on both sides of the porous membrane in the fabricated device by flowing cell suspensions. Specifically, bEnd.3 (endothelial) and C8D1A (astrocyte) cell lines were employed utilizing standard mammalian tissue culture methods.

The fabricated µBBB platform was sterilized and adhesion-seeded by steadily perfusing for up to seven days. Gas-permeable manifold tubing (0.25 mm ID) was attached to 22½ gauge needles and 10 ml pipet tips. Tips were sealed to the inlet holes with silicone sealant (DC734), and chips were connected to a 205S peristaltic cartridge pump (Watson-Marlow) for fluid manipulation. 250 ml 8-well strips were used as reservoirs, covered with gas-permeable TFE/silicone plugs (BioTech Solutions). Chips were perfused with 70% ethanol to prevent contamination. To facilitate cell adhesion, the membrane was coated with 10 mg $ml^{-1}$ fibronectin for 2 h, then filled with growth medium and fully cleared of bubbles prior to cell seeding.

Next, the platforms were first seeded on the abluminal side with astrocytes at the concentration of $6e^4$ $cm^{-2}$ by flooding concentrated cell suspension ($3e^6$ $ml^{-1}$) in the abluminal chamber and inverting the devices at zero flow for two hours. Before seeding endothelial cells, the μBBB was perfused with medium at 1.3 ml min$^{-1}$ for two days.

Then, bEnd.3 cells were secondly seeded at the concentration of $6e^4$ cm$^{-2}$ in the luminal channel and allowed to adhere for two hours before rinsing with medium perfused at 1.3 ml min$^{-1}$ for 12 h, followed by 2.6 ml min$^{-1}$.

Note that cells used for seeding BBB models were taken from confluent cultures (after day 3 after passage) only. Static BBB models were also tested for comparison by seeding astrocytes at $6e^4$ cm$^{-2}$ on the underside of transwells (Corning) pre-treated with 10 pg ml$^{-1}$ human fibronectin (Cultrex) in PBS for 2 h and allowed to adhere for 2 h, then cultured for 2 days prior to endothelial cell seeding on the topside at $6e^4$ cm$^{-2}$.

All cell cultivation and BBB experiments, including the devices and pump assembly, were carried out in a Nu-Aire Autoflow 4750 incubator which maintains a constant interior environment at 5% $CO^2$ and 37° C., as indicated by internal temperature and $CO^2$ sensors in the incubator, with certified accuracies of +0.0125° C. and +0.1%, respectively. Cell suspensions were centrifuged in an Eppendorf 5810, and sterile work was done in a class II biosafety cabinet (Thermo Fisher). Media used for all procedures was DMEM:F12 (CellGro), supplemented with 10% FBS (Hyclone), 1% Penicillin/Streptomycin, and 1% Fungizone (EMD). Media was buffered (NaOH or HCl buffers) to pH 7.4 (VWR sympHony) and sterile-filtered for all experiments, except for experiments in which media was buffered to pH 10. All media was supplemented with 1.2 g L$^{-1}$ sodium bicarbonate to minimize changes in pH, though any changes in pH over the course of μBBB experiments were not measured due to volume limitations of the pH meter. The endothelial cell line bEnd.3 and astrocytic cell line C8-D1A were received from ATCC.

Exemplary Device Testing Methodology

To evaluate the fabricated μBBB system, three methods were employed: (1) Cell imaging to observe structure and morphology, (2) TEER levels to evaluate cell confluence and tight junction integrity, and (3) permeability assays to evaluate barrier selectivity. Cells were imaged with a Live/Dead assay to verify cell viability, and immunostained to look at expression of astrocyte marker GFAP and tight junction component zonal occluding-1 (ZO-1). TEER was measured as an indicator of cell confluence and tight junction integrity, with time to maximum TEER being indicative of BBB development time. Fluxes of fluorescent-labeled tracer molecules were measured to assess permeability to larger solutes. To observe the system's response to environmental changes, cells were exposed to histamine during TEER measurement and high pH during permeability assays. Real-time TEER was measured in co-cultured μBBB models during exposure to histamine (Calbiochem) at 100 μM and 150 μM (micro Molar) concentrations. Permeability was measured in μBBB models exposed to DMEM:F12 media with elevated pH (>10) for 4 h.

Imaging

Light-phase and ESEM imaging were used for morphological observations, Live/Dead assay was used to assess viability, and immunostaining was used to look at expression of glial and tight junction marker proteins GFAP and ZO-1. To assess viability of cultured cells, Live/Dead (MGT) solution was incubated for 90 min and imaged using a Nikon fluorescence microscope. For immunostaining of both cell types, cells were fixed with 4% paraformaldehyde (Avantor) for 10 min at room temperature. Cells were permeabilized with 0.1% Triton X-100 in PBS for 10 min and blocked with 5% goat serum (Rockland) and 1% unconjugated goat anti-mouse IgG F(ab')$_2$ fragment (ImmunoPure) in permeabilization buffer for 1 h. Cultures were incubated with primary antibody in blocking solution overnight at 4° C. Cultures were rinsed with blocking solution and left in secondary antibody for 1 h, counter-stained with DAPI (Enzo) for 5 min, and imaged with a Nikon fluorescence microscope. Mouse anti-ZO-1 (Invitrogen) was used in conjunction with Alexa Fluor 488 goat anti-mouse secondary antibody (Invitrogen). Rabbit anti-GFAP (Invitrogen) was used in conjunction with Alexa Fluor 488 goat anti-rabbit secondary antibody (Invitrogen). For imaging with environmental SEM (FEI Quanta 600 FEG), astrocyte cultures were rinsed and fixed in 4% paraformaldehyde solution for 24 h at 4° C.

TEER Measurement

Over the course of the μBBB model evaluation experiments, TEER was measured twice a day to monitor cell confluence and development of tight junctions. For measurement of TEER, voltage and current electrode wires were connected via an electrode adaptor (WPI) to an EVOM2 epithelial voltohmmeter (WPI). The EVOM2 passes a constant 10 μA AC current at 12.5 Hz while measuring resistance. To calculate TEER, initial D0 Background resistances $R_b$ were subtracted from total resistance $R_C$ at each time point and normalized for area, giving TEER values in Ωcm$^2$ as in the following equation:

$$TEER = (R_C - R_b)A$$

For real-time data collection during histamine exposure, the EVOM2 was connected to LabView on a PC via a data acquisition device (Texas Instruments). TEER of transwell cultures were measured daily by placing them in an Endohm chamber (WPI) and connecting it to the EVOM2.

Permeability

To assess barrier permeabilities to large compounds, fluxes of fluorescent tracers over a wide range of sizes were measured after steady-state TEER had been reached under each variant condition: monolayer, co-culture, and co-culture with elevated pH. The permeability of the system to dissolved compounds is detected by measuring the rate of diffusion across the membrane. After day 3 of endothelial culture, FITC-Dextrans 4k, 20k, 70k (Sigma), and propidium iodide (Biotium) were passed at a concentration of 500 mg ml$^{-1}$ in media through the luminal channel of each device, and blank media was passed through the abluminal channel. The level of fluorescence in the media collected from the abluminal channels were measured using a BioRad Synergy Plate Reader, and converted to concentration according to prepared standards. Solute flux $J_s$ was calculated by dividing concentration change by assay time. Permeability coefficients were calculated using the following equation for permeability:

$$P = \frac{J_s}{AC_L}$$

Where P is the permeability coefficient, $J_s$ is solute flux across the membrane, A is membrane area, and $C_L$ is concentration on the luminal (source) side of the membrane. Epithelial coefficients $P_e$ were calculated by subtracting the inverse of the overall P value by the inverse of coefficient $P_b$ from a blank membrane, as in the following equation for permeability normalization.

$$\frac{1}{P_e} = \frac{1}{P} - \frac{1}{P_b}$$

All permeability assays were conducted after day 3 of endothelial culture. Assays were conducted for both monolayer and co-cultured devices. To evaluate the effect of pH elevation on permeability, assay was repeated with cultures exposed to media containing pH>10 for 4 h.

Results of Exemplary Device Testing

The measurements indicated the validity of the developed μBBB model as an in vitro model system for studies of barrier function and drug delivery. Characteristics of a valid in vitro BBB model may include: practicality and ease of use, in vivo-like cell morphology, functional expression of BBB-specific proteins, and a restricted paracellular pathway as indicated by high TEER and low permeability to compounds. The bEnd.3 cell line has been previously characterized as having acceptably high functionality of P-glycoprotein transporter, as well as expression of numerous transporters. Finally, the restrictive paracellular pathway was demonstrated by TEER levels over 250 $\Omega cm^2$ and tracer permeabilities comparable to other BBB models.

Imaging

Figure 3A:
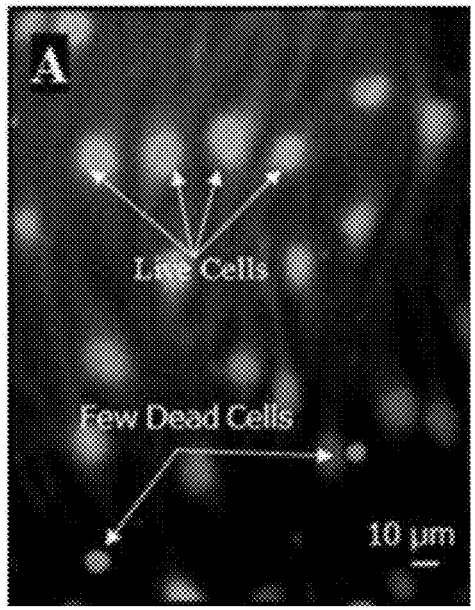
FIG. 3A is a Live/Dead stain of bEnd.3 cells on day 3 of culture on a μBBB membrane.
Figure 3B:
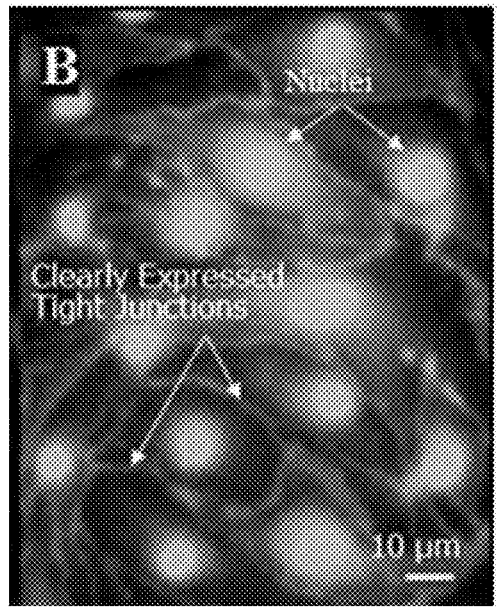
FIG. 3B shows immunostains of tight junction component ZO-1 in bEnd.3 cells on day 3 of culture on a μBBB membrane.
Figure 3C:
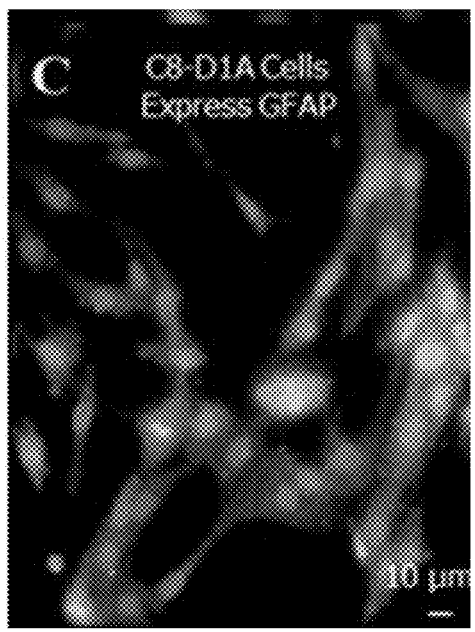
FIG. 3C shows immunostains of GFAP in C8-D1A cells.
Figure 3D:
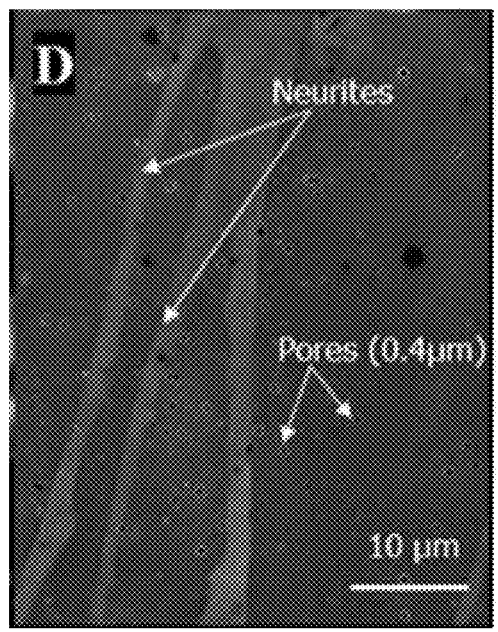
FIG. 3D is an ESEM of C8-D1A neurites on a porous polycarbonate membrane.

Imaging results were indicative of in vivo like morphologies for both cell types, validating structural requirements for BBB. FIGS. 3A-3D are representative images of cells obtained while testing the μBBB model. Specifically, FIG. 3A is a Live/Dead stain (as indicated) of bEnd.3 cells on day 3 of culture on μBBB membrane indicating high cell viability. FIG. 3B show immunostains of tight junction component ZO-1 (as indicated) in bEnd.3 cells on day 3 indicating distinct tight junction expression. Nuclei are counter-stained with DAPI. FIG. 3C are immunostains of GFAP in C8-D1A cells revealing astrocytic morphology on polycarbonate membrane. Nuclei are counter-stained with DAPI. FIG. 3D is an ESEM of C8-D1A neurites on the porous polycarbonate membrane.

Results from Live/Dead assays conducted on day 3 of endothelial culture on μBBB membranes indicated high cell viability (>90%) of endothelial cells cultured in the system (FIG. 3A). Similar cell survival was seen for astrocytes cultured in the system. Immunostains of bEnd.3 cells cultured in the system revealed distinct expression of tight junction component ZO-1 by day 3 of culture (FIG. 3B). Immunostains on day 2 typically lacked as clearly distinct expression of ZO-1 as seen on day 3-4, suggesting a three day period for full barrier development in some embodiments, consistent with the TEER results. Evaluation of the endothelial monolayer structure of bEnd.3 cells confirmed previous analysis on the cell line as valid for BBB models, in that tight junctions were expressed by day 3 of culture in the system, even without astrocyte co-culture.

Morphological analysis of the C8-D1A cell line was necessary due to a lack of described previous models using the cell line. The C8D1A cell line regularly expressed an astrocytic morphology with distinct neurites. Immunostains of C8D1A cells revealed expression of GFAP, which is a marker specific to astrocytes (FIG. 3C). ESEM of astrocytes cultured on polycarbonate membrane revealed good adhesion to the substrate (FIG. 3D), though the neurites were typically wider (>1 μm) than the pore diameter (0.4 μm), so it is unlikely that endfeet were able to migrate through the pores of the membrane used. Embodiments utilizing membranes with larger pores, as described above, are also within the scope of the present disclosure.

The experimental setup was small enough for the entire pump system to be placed in the incubator and kept at 37° C., and up to 4 devices could be run simultaneously with an 8-channel pumphead during testing. Imaging indicated that both cell types exhibited characteristics desirable for BBB study, and cells were co-cultured in close contact.

TEER

Figure 4A:
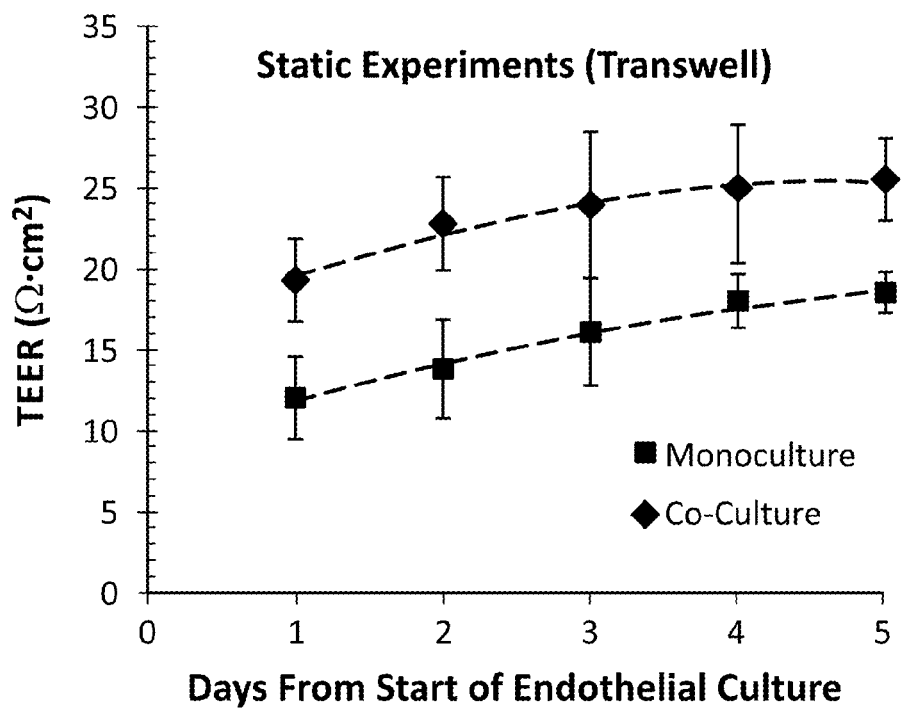
FIG. 4A is a graphical representation of TEER levels over time in transwells seeded with bEnd.3 cells in monoculture and in co-culture with astrocytes.
Figure 4B:
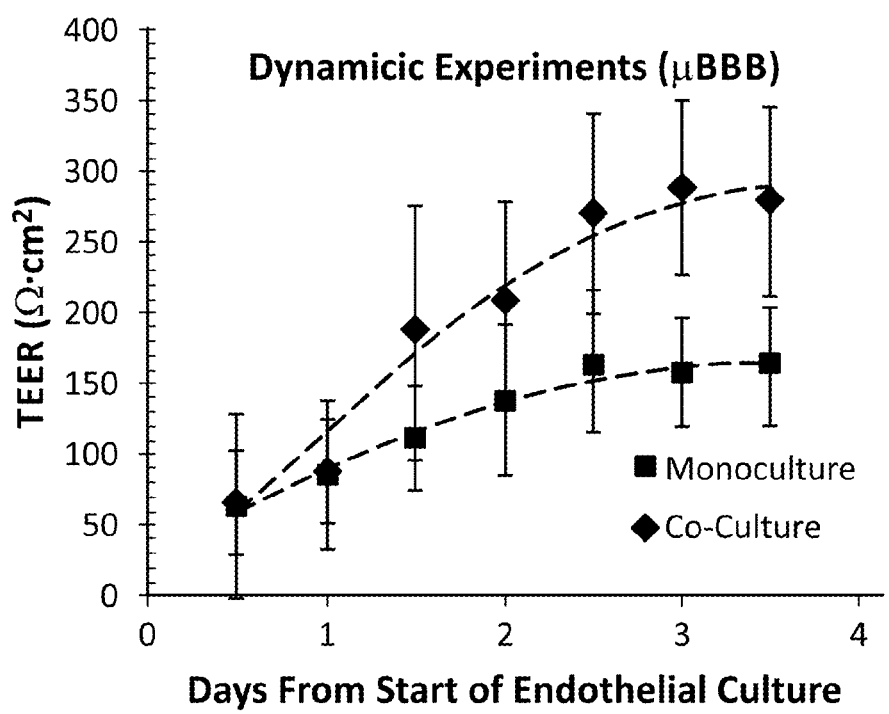
FIG. 4B is a graphical representation of TEER levels over time in μBBB devices seeded with bEnd.3 cells in monoculture and in co-culture with astrocytes.

TEER results indicated high electrical resistance, with conveniently short time to steady-state TEER levels, and demonstrated a transient response to histamine. For both static transwell experiments and dynamic μBBB cultures, cultures typically reached steady-state levels by day 3-4 of endothelial cell culture as shown in FIGS. 4A-4B, which are graphical representations of TEER levels over time. These measurements were indicative of full tight junction development, in congruence with the ZO-1 imaging data, so, in the tested embodiment, day 3 was the threshold for endpoint testing such as permeability assays, immunostains, and TEER response assays. For both systems, co-culturing endothelial cells with astrocytes increased the steady-state TEER levels, as indicated by the arithmetic means over several runs as shown in FIGS. 4A-4B. Specifically, FIG. 4A shows TEER development of transwells seeded with bEnd.3 cells in monoculture and in co-culture with astrocytes, while FIG. 4B shows TEER development of μBBB devices seeded with bEnd.3 cells in monoculture and in co-culture with astrocytes. All n>3 in these figures.

Figure 5:
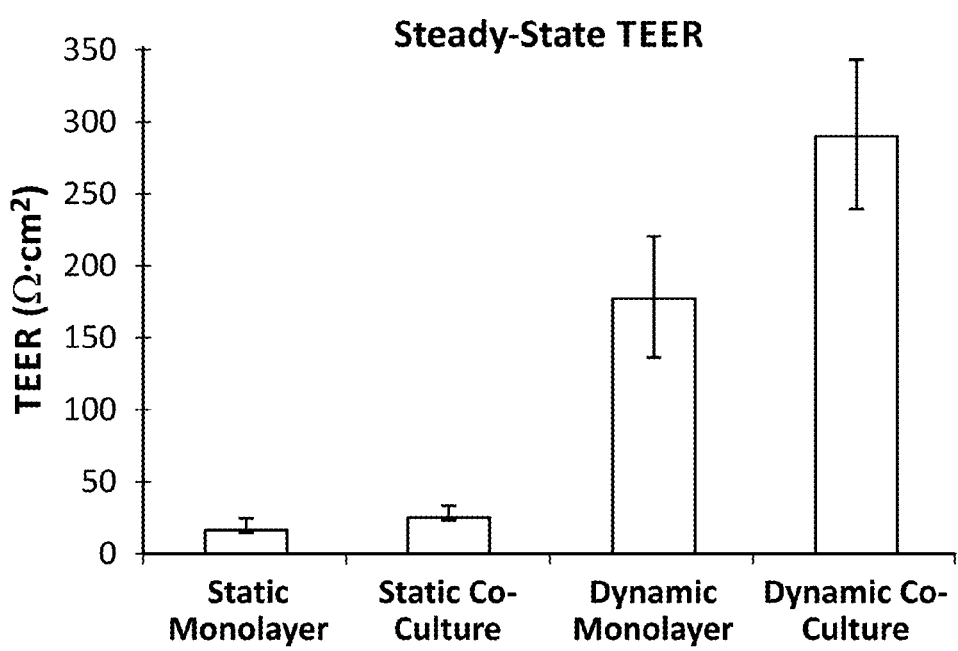
FIG. 5 is a graphical representation of steady-state TEER levels at various base conditions.

Steady-state TEER measurements. The steady-state TEER values in the dynamic μBBB chips were higher than the static transwell controls using the same cell lines, media formulations, and voltohmmeter. These data are shown in FIG. 5, which is a graphical representation of steady-state TEER levels of each base condition. Again, as shown in FIG. 5, the dynamic cultures reached higher TEER levels than static cultures. For both systems, co-cultures developed higher TEER levels than endothelial monolayers alone. TEER levels of μBBB co-cultures regularly exceeded 250 $\Omega cm^2$, compared to only 25 $\Omega cm^2$ in transwell co-cultures. It appears that this increase in TEER may be due to the effects of shear stress on endothelial cells. Shear stress may have a mechanotransductive effect on endothelial molecular pathways, and may be seen to up-regulate expression of tight junction proteins and increase RNA levels of BBB transporter proteins in vascular endothelial cells, modulate cytoskeletal structure, and shows less inflammatory effects with definitive directional flow than disturbed flow.

Additional differences observed between the μBBB system and the transwell controls which may factor into differences in results, include: total cell numbers and media volumes, culture surface/volume ratios, ratio between endothelial cells and astrocytes, and TEER electrode characteristics such as size, gap, and orientation.

Though in vivo TEER levels are greater than 1000 $\Omega cm^2$, for a system showing sufficiently high TEER levels over 150 $\Omega cm^2$, reasonably representative data can be obtained. The μBBB system may in some versions exceed 250 $\Omega cm^2$.

Figure 6A:
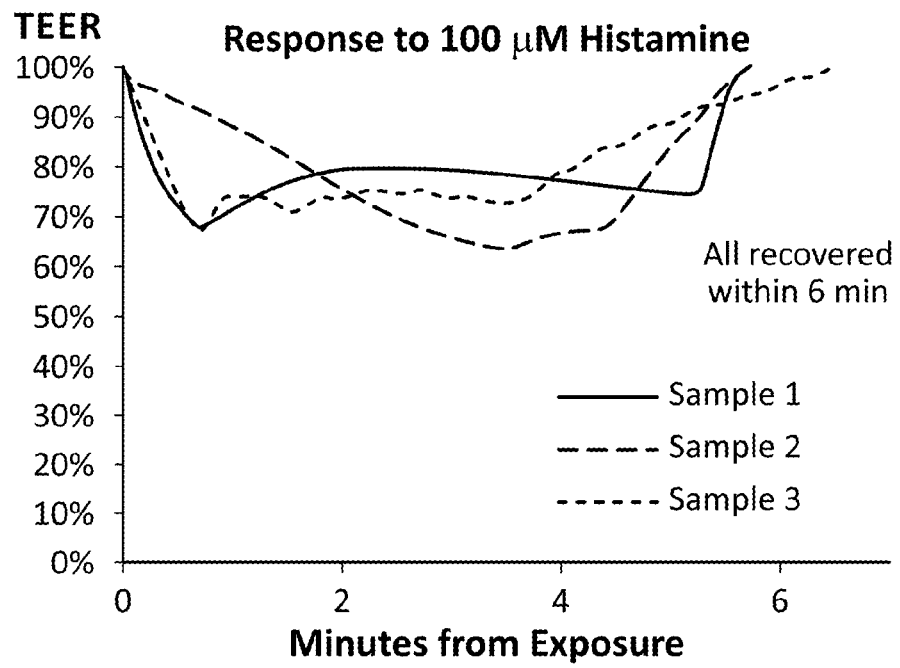
FIG. 6A is a graphical representation of a continuous response to histamine exposure in three samples at a first concentration.
Figure 6B:
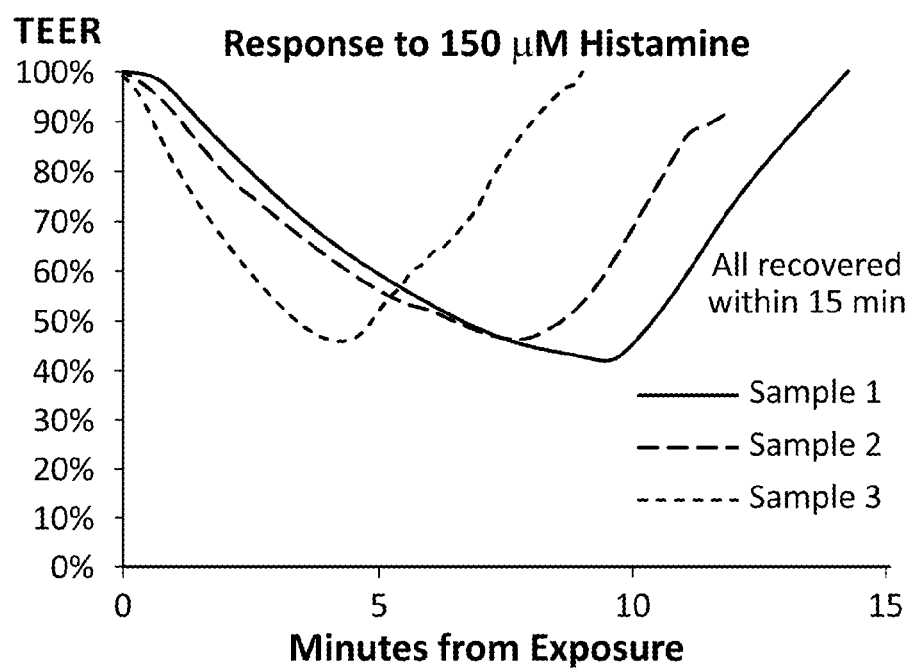
FIG. 6B is a graphical representation of a continuous response to histamine exposure in three samples at a second concentration.

Dynamic TEER measurements. A transient drop and recovery to the original levels in TEER was also observed as a result of exposure to histamine, as shown in FIGS. 6A and 6B. FIGS. 6A and 6B are graphical representations of a continuous response to histamine exposure in three samples at two concentrations. Co-cultured μBBB models on day 4 were perfused with histamine at two concentrations: as shown in FIG. 6A, three samples perfused with 100 μM histamine saw a transient drop of up to 30% over a period of 5-7 min, and as shown in FIG. 6B, three samples perfused with 150 μM histamine saw a transient drop of up to 50% over a period of 8-15 min.

The data of FIGS. 6A and 6B may indicate the robustness of the model for repeated and long-term testing purposes. The drop occurred rapidly upon exposure to histamine, and TEER returned to initial levels within six minutes at 100 μM histamine concentration, and 15 minutes for 150 μM concentrations. Maximum TEER drop was approximately 30% for 100 μM histamine, and 50% for 150 μM histamine. This effect may be attributed to brief formation of trans-endothelial gap formation, and may also be due to increased transcytosis. The ability to observe real-time transient changes in TEER without disturbing the system may be a significant practical characteristic of the present system not available in other models.

Permeability

Figure 7:
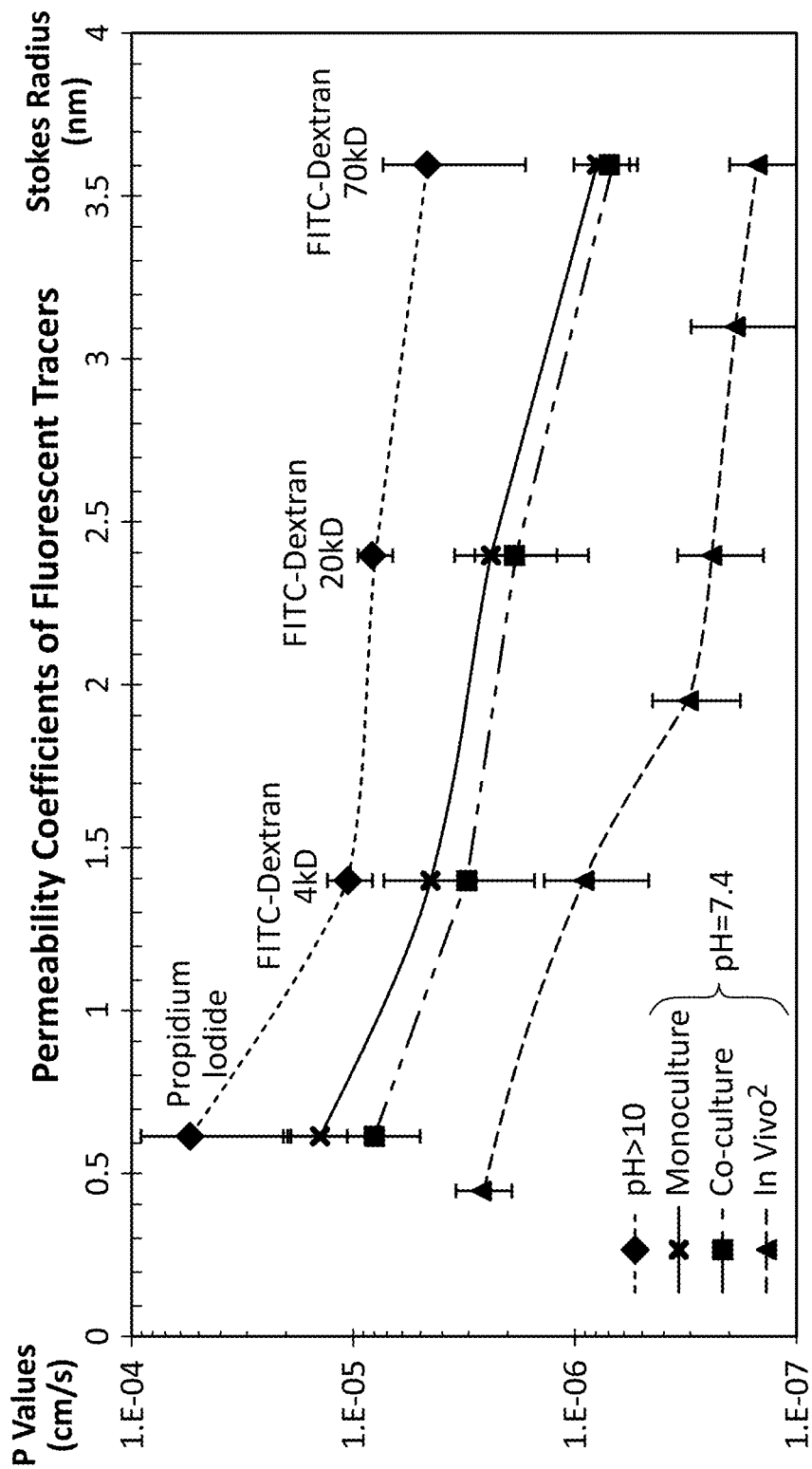
FIG. 7 is a graphical representation of permeabilities of cultured μBBB under different tracer (molecular) sizes.

Permeabilities of μBBB cultures to large molecules were shown to be selective according to size, and seen to be slightly lower for co-cultures than endothelial cells alone, and found to be higher when pH was significantly elevated. The μBBB system may be advantageous for permeability assays, because the permeability equation above assumes tracer concentrations are kept constant, which is not necessarily true for static models in which concentrations in both chambers change with time. This is a valid assumption for flow-based BBB models, because fresh media at constant concentration may be continuously delivered to the chamber. Permeability coefficients of Dextrans 4 kD, 20 kD, and 70 kD, and propidium iodide were calculated and plotted according to stokes radius, or the radius of a sphere with the same diffusive properties, as shown in FIG. 7. FIG. 7 is a graphical representation of permeabilities of cultured μBBB under different conditions. Tracer molecules FITC-Dextrans 4k, 20k, 70k, and propidium iodide reveal selectivity according to size. Also plotted for reference is in vivo data from another study (W. Yuan, Y. Lv, M. Zeng and B. M. Fu, *Microvasc. Res.*, 2009, 77, 166-73), which showed a lower permeability curve than all in vitro models. Co-cultures showed lower permeability than monocultured bEnd.3 cells alone. Furthermore, increasing pH to 10 for 4 h resulted in increased permeabilities. In FIG. 7, all n>3.

Again referring to FIG. 7, results for all conditions showed higher permeability to tracers of lower stokes radius, indicating that smaller compounds may pass through junctions easier. Co-cultured systems showed lower permeability than for monoculture of endothelial cells alone, consistent with the higher TEER levels. Exposing μBBB co-cultures to higher pH levels (>10) for 4 h led to higher permeabilities to all tracers, indicating loss of barrier function. This increase in permeability due to heightened pH may be indicative of a drop in barrier function. However, permeabilities for both co-cultures and endothelial monoculture were higher than those previously reported from in vivo studies, as shown in FIG. 7, which is consistent with the higher TEER measurement for these conditions. No BBB model displayed permeability levels as low as in viva In some embodiments, a single chip may comprise multiple fluid pathways of differing sizes or geometries. In some such embodiments, the fluid pathways may have a common inlet and/or a common outlet. Such a structure may allow for an array of parallel channels, which may correspond to an array of parallel test parameters. For example, the luminal channel (such as 125 of FIG. 1) may be divided into multiple branches or channels, each with differing geometries. This may allow differing flow rates, shear stresses, and volumes within each channel. The branches may all have a common inlet and outlet, and may each intersect with a common abluminal channel (such as 135 of FIG. 1). Such a design may facilitate simultaneous use of various differing test parameters (such as shear stress and/or flow) while keeping other parameters constant across each parallel channel (such as the composition of the fluid within the channel). In other embodiments, multiple abluminal channels may be utilized and multiple inlets or outlets may be included.

Parallel arrays may facilitate simultaneous testing or evaluation of the μBBB model at various shear stresses. Shear stress may have a mechanotransductive effect on a myriad of endothelial molecular pathways by activating membrane-bound integrins and receptor tyrosine kinases. These pathways may increase gene and protein expression leading to increased tight junction proteins such as ZO-1 and modulation of cytoskeletal structure, promoting cell reorientation and restructuring—factors which influence permeability and TEER in the BBB (and the μBBB model). In some instances, use of parallel arrays may facilitate testing or evaluation of a wide span of shear stress, such as a 100× ratio, for example.

In one exemplary procedure, to quantitate the increases in TEER under various shear stresses, a modified μBBB model comprising parallel arrays of channels with varying widths, resulting in variable shear stress in individually monitored channels, was designed as outlined below.

Figure 8A:
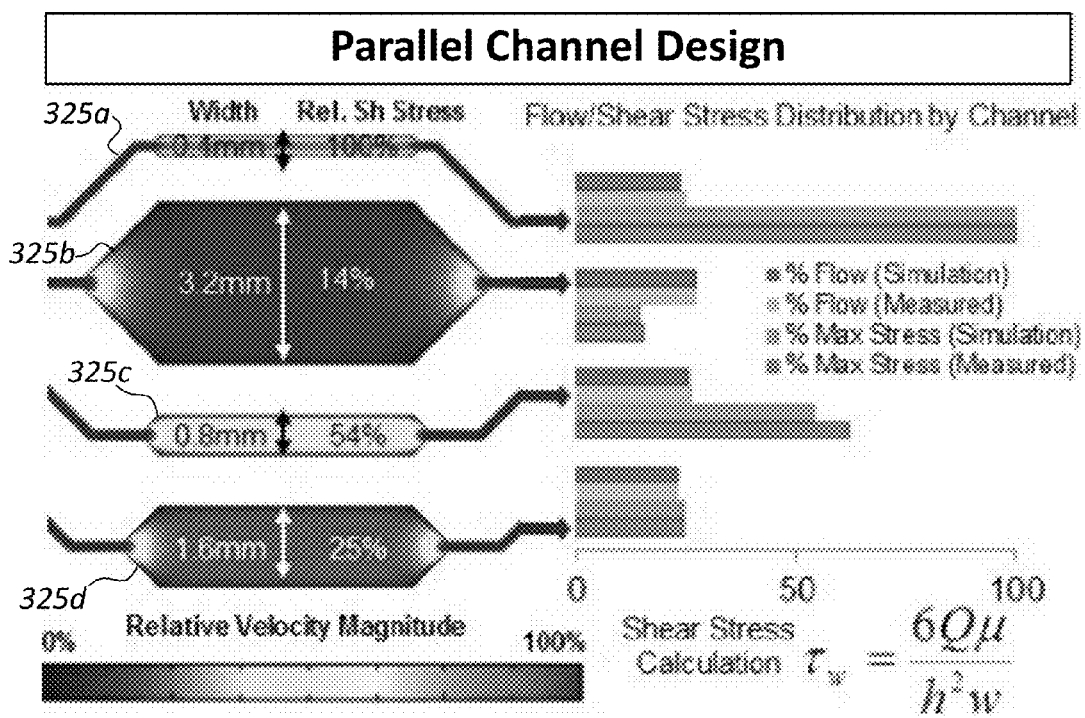
FIG. 8A is a schematic illustration of luminal flow channels of another embodiment of a μBBB enhancing the ranges of flow rates in a massively-parallel array.

FIG. 8A is a schematic illustration of the modified μBBB model used in this example. Four luminal channels 325a, 325b, 325c, and 325d, each having different dimensions, are shown. Each of these channels intersected with a common abluminal channel in the exemplary device. The device used in this example was fabricated as follows.

Sputtered Cr/Au/Ag (20/80/800 nm) was deposited onto a glass substrate and patterned using liftoff (LOR-10B), and AgCl was generated with 30 mM $FeCl_3$ (50 s). Channel molds were patterned with SU-8 2075, and PDMS was cast with glass electrode layers embedded and cured (60° C.). Polycarbonate sheets (0.4 μm pores, 10 μm thick) were cut from transwells (Corning) and bonded between channel layers with 50:50 PDMS pre-polymer:toluene. Marprene or silicone tubing (0.25 mm, 0.38 mm) was sealed (DC734) to input holes, and used with a 205S cartridge pump (Watson-Marlow). Devices were sterilized (70% eth), membranes were coated with poly-D-lysine (10 μg/ml, 6 h on bottom), and fibronectin+collagen IV (10 μg/ml, 2 h on top), then seeded with C8D1A astrocytes in the common channel ($6e^4/cm^2$, 2 h). After two days, bEnd.3 brain endothelial cells were seeded in parallel channels ($6e^4/cm^2$, 2 h). DMEM:F12 was circulated at near-static flow-rates overnight, subsequently followed by experimental flow-rates. TEER was measured with an EVOM2 (WPI). To test the permeability at these flow conditions in a single-channel μBBB, fluxes of FITC-dextran (4 kD, 20 kD, 70 kD), propidium iodide, and FITC-G4 dendrimers across the membrane were measured (BioRad Synergy) and permeability coefficients were calculated.

Figure 8B:
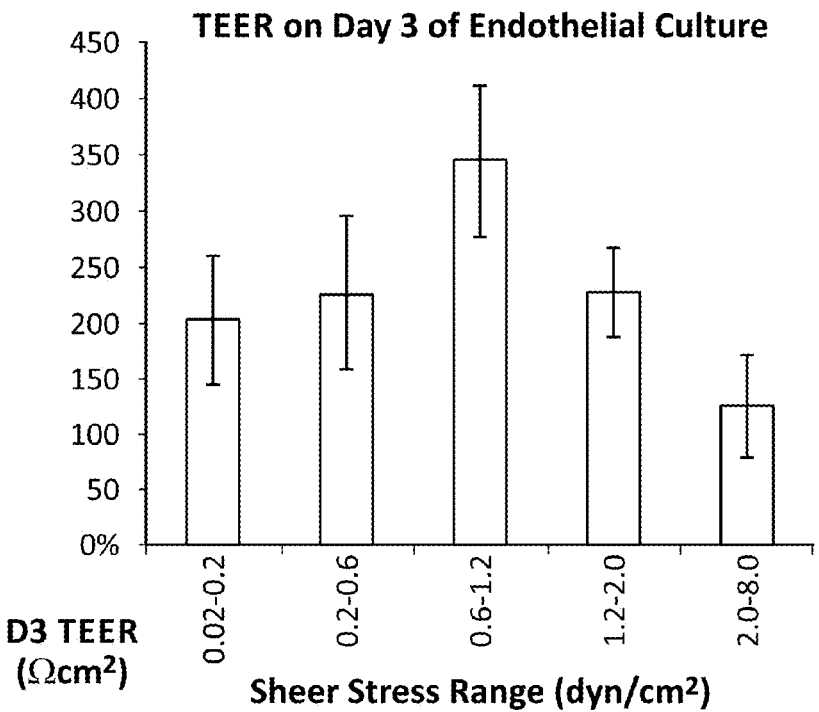
FIG. 8B is a graphical representation of Day 3 TEER at varying shear stress rates, in one exemplary test of the μBBB represented in FIG. 8A.
Figure 8C:
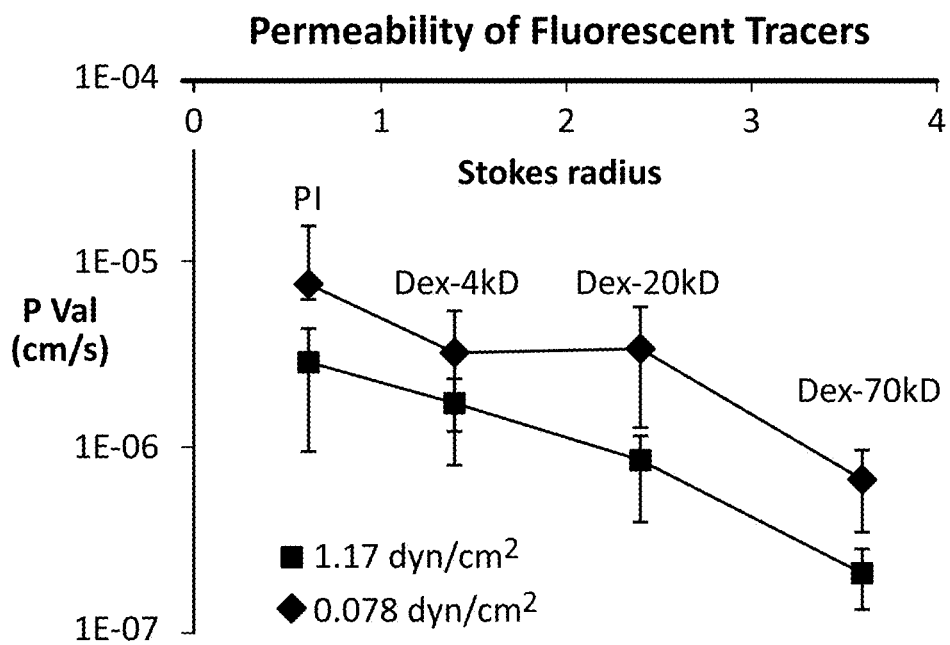
FIG. 8C is a graphical representation of permeabilities of fluoro-tagged tracers in the exemplary test referenced in FIG. 8B.
Figure 8D:
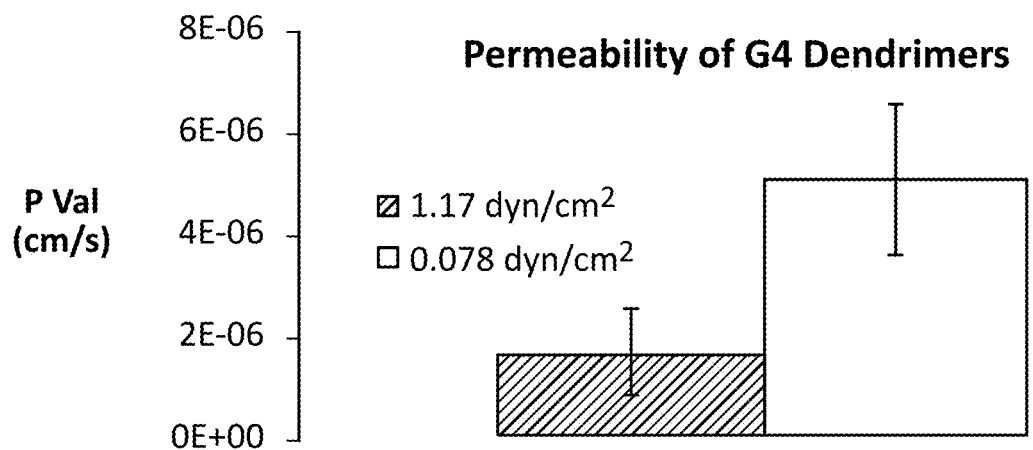
FIG. 8D is a graphical representation of permeability of PAMAM Dendrimer drug carriers (G4, FITC-tagged) in the exemplary test referenced in FIG. 8B.

Day 3 TEER for channels exposed to shear stress ranging 0.6-1.2 $dyn/cm^2$ was higher than those under 0.2 $dyn/cm^2$ and over 1.2 $dyn/cm^2$, with particular drop-off over 2 $dyn/cm^2$, as shown in the graphical representation of FIG. 8B. This drop-off may be due to limitations of cell adhesion to the membrane. Permeabilities of fluorescent tracers through single-channel μBBBs were lower at stress at optimal TEER (1.2 $dyn/cm^2$) than at 0.078 $dyn/cm^2$, as represented in FIG. 8C. These results may indicate that optimal barrier function of μBBB is achieved at shear stress of 1.2 dyn/cm$^2$, which falls into the range of physiological shear stresses (1-60 dyn/cm$^2$) found in vivo. Permeability of PAMAM Dendrimer drug carriers (G4, FITC-tagged) also show a decrease 1.17 dyn/cm$^2$ shear stress, as represented in FIG. 8D.

Figure 9A:
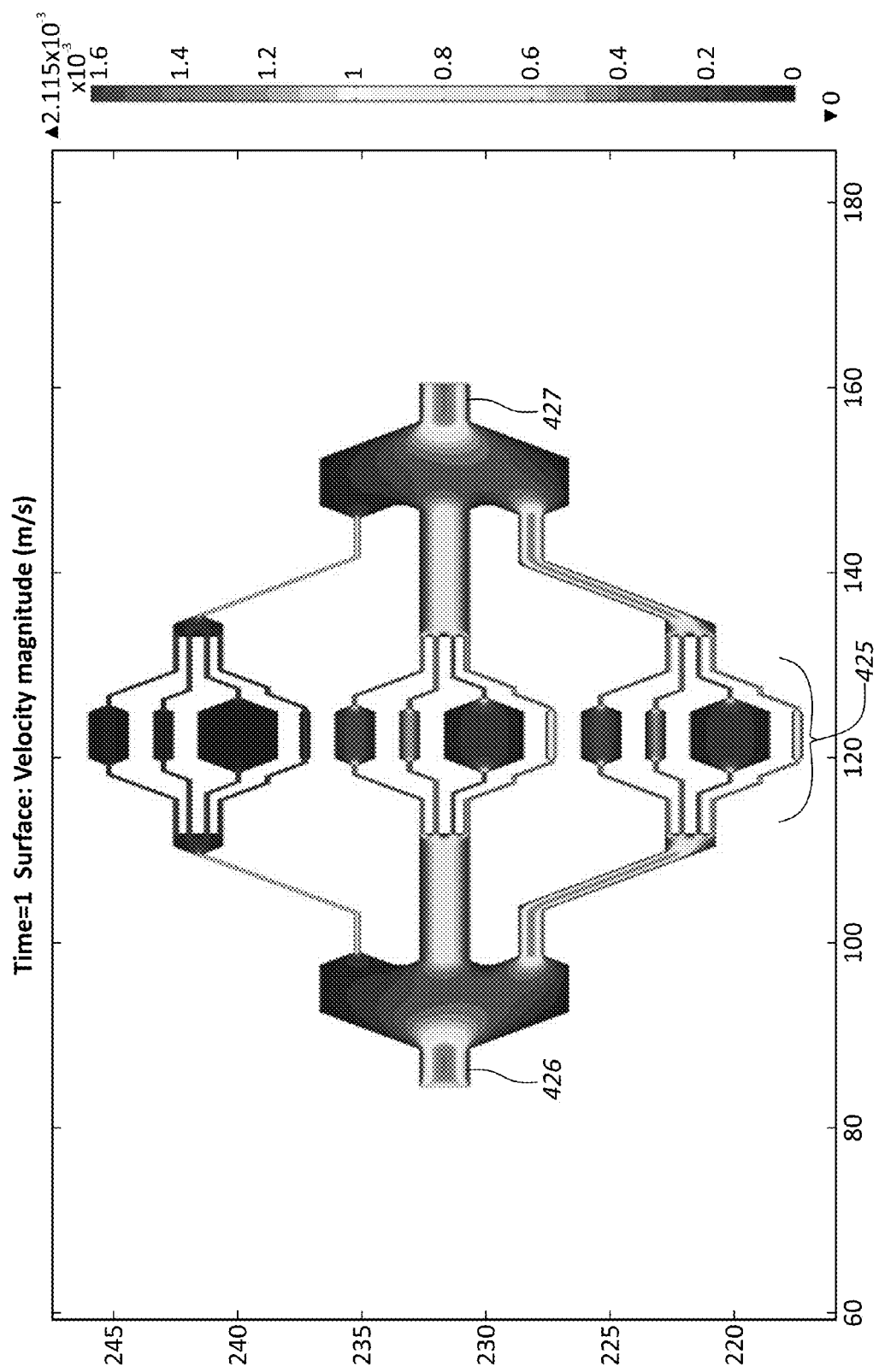
FIG. 9A is a schematic representation of luminal flow channels of another embodiment of a μBBB in a multiple state to induce a wider range of flow conditions.
Figure 9B:
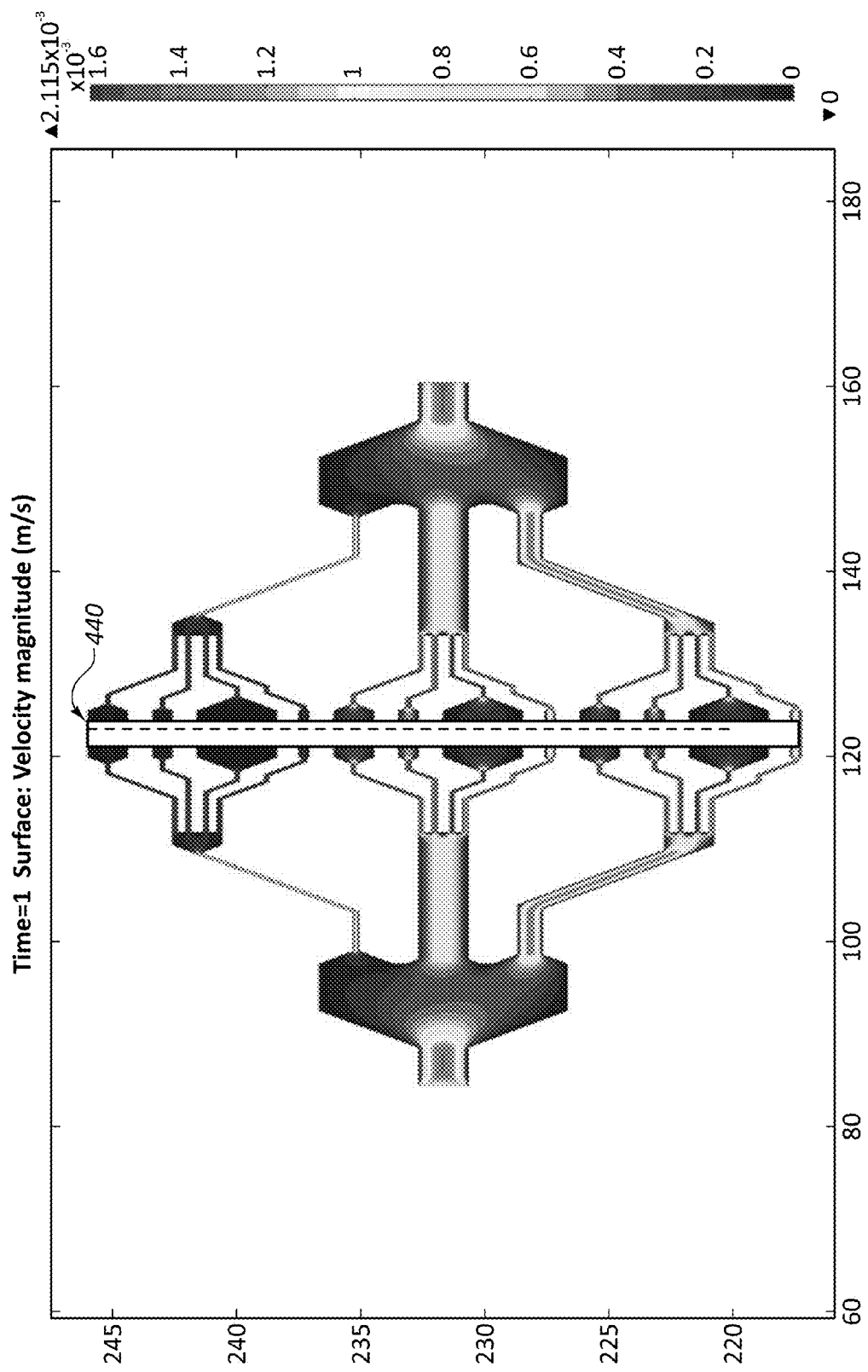
FIG. 9B is a schematic representation of the luminal flow channels of the embodiment of FIG. 9A with the location of the cell-membrane interface illustrated.

FIG. 9A is a schematic representation of another pattern of parallel luminal channels 425 having a common inlet 426 and a common outlet 427. Each of these channels 425 may intersect with a common abluminal channel or they may be associated with multiple abluminal channels. FIG. 9B is another reproduction of the schematic view of FIG. 9A, with the approximate location of the cell-membrane intersection 440 for each channel indicated.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. A biological barrier model comprising:
   a first microfluidic channel comprising a plurality of separate branch channels, wherein at least one of the separate branch channels differs in width from the width at least one other branch channel;
   a second microfluidic channel that is set crosswise relative to each branch channel of the plurality of separate branch channels; and
   one or more semipermeable membranes disposed between the first microfluidic channel and the second microfluidic channel to form a plurality of interfaces, wherein each interface of the plurality of interfaces is disposed between a branch channel of the plurality of branch channels and the second microfluidic channel.

2. The biological barrier model of claim 1, wherein both the first microfluidic channel and the second microfluidic channel are about 200 μm high.

3. The biological barrier model of claim 2, wherein the interface of at least one of the interfaces is about 2 mm wide and the second microfluidic channel is about 5 mm wide at the interface.

4. The biological barrier model of claim 2, wherein the interface of at least one of the interfaces is about 2 mm wide and the second microfluidic channel is about 2 mm wide at the interface.

5. The biological barrier model of claim 1, wherein the first microfluidic channel is configured to promote uniform shear stress on a first layer of cells cultured on a first surface of the one or more semipermeable membranes, and wherein the first microfluidic channel has an aspect ratio of at least 10:1.

6. The biological barrier model of claim 1, further comprising:
   a first culture of cells on a first surface of the one or more semipermeable membranes, wherein the first surface is in fluid communication with the first microfluidic channel; and
   a second culture of cells on a second surface of the one or more semipermeable membranes, wherein the second surface in fluid communication with the second microfluidic channel.

7. The biological barrier model of claim 6, wherein the first culture of cells comprises endothelial cells and the second culture of cells comprises astrocytes, and wherein the one or more semipermeable membranes are configured to promote cell to cell interactions between the endothelial cells and the astrocytes.

8. The biological barrier model of claim 7, wherein the one or more semipermeable membranes are no more than 10 μm in thickness, and wherein the one or more semipermeable membranes comprise pores of no less than 0.4 μm in diameter.

9. The biological barrier model of claim 7, wherein the endothelial cells comprise a bEnd.3 cell line and the astrocytes comprise a C8D1A cell line.

10. The biological barrier model of claim 1, further comprising a first electrode in fluid communication with the first microfluidic channel and a second electrode in fluid communication with the second microfluidic channel.

11. The biological barrier model of claim 10, wherein the first electrode is disposed within about 200 μm of a first culture of cells and the second electrode is disposed within about 200 μm of a second culture of cells.

12. The biological barrier model of claim 6, wherein the biological barrier model achieves steady-state TEER levels in three days, and wherein TEER levels exceed 250 Ωcm$^2$ at steady-state.

13. The biological barrier model of claim 1, wherein each branch channel is configured such that each branch channel induces a different shear stress in response to fluid flow from a common inlet, and wherein the shear stress in each branch channel is controlled by the fluid flow rate through each branch channel.

14. The biological barrier model of claim 1, wherein the first microfluidic channel is oriented such that fluid flow through each branch channel of the plurality of branch channels is angled relative to fluid flow through the second microfluidic channel.

15. The biological barrier model of claim 1, wherein the second microfluidic channel is unbranched.

* * * * *